US008167986B2

(12) United States Patent
Schneider et al.

(10) Patent No.: US 8,167,986 B2
(45) Date of Patent: May 1, 2012

(54) AIRBORNE PARTICULATE SAMPLER

(75) Inventors: Raymond W. Schneider, Baton Rouge, LA (US); Erik Durr, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 423 days.

(21) Appl. No.: 12/506,603

(22) Filed: Jul. 21, 2009

(65) Prior Publication Data

US 2010/0075317 A1    Mar. 25, 2010

Related U.S. Application Data

(60) Provisional application No. 61/082,977, filed on Jul. 23, 2008.

(51) Int. Cl.
*B03C 3/15* (2006.01)

(52) U.S. Cl. ............. 96/61; 95/78; 95/81; 96/63; 96/83; 96/97

(58) Field of Classification Search ................ 96/61, 63, 96/80, 83, 97–99; 95/78, 80, 81; 73/863.21, 73/863.22
See application file for complete search history.

(56) References Cited

U.S. PATENT DOCUMENTS

| | | | | |
|---|---|---|---|---|
| 1,995,790 A | * | 3/1935 | Anderson | ........................... 96/64 |
| 2,381,578 A | * | 8/1945 | Dillon et al. | ...................... 95/57 |
| 4,041,768 A | * | 8/1977 | Gibert et al. | .................. 73/24.03 |
| 4,976,752 A | * | 12/1990 | Torok et al. | ........................ 96/43 |
| 5,243,864 A | | 9/1993 | Dunmyre et al. | ........... 73/864.71 |
| 5,762,691 A | * | 6/1998 | Gondar | ............................. 96/60 |

(Continued)

FOREIGN PATENT DOCUMENTS

JP    5-161859 A  *  6/1993    ........................ 96/97

OTHER PUBLICATIONS

Grinshpun, S.A. et al., "A small change in the design of a slit bioaerosol impactor significantly improves its collection characteristics," *J. Environ. Monit.*, vol. 9, pp. 855-861 (2007).

(Continued)

*Primary Examiner* — Richard L Chiesa
(74) *Attorney, Agent, or Firm* — John H. Runnels; Bonnie J. Davis

(57) ABSTRACT

An airborne particulate sampling device is disclosed. The device includes a conduit whose interior allows the flow of air through the device. The conduit, or at least its surface, is a conductor. The device also includes an electrode with a sharp tip or edge on or near the output side of the conduit. An electrically conducting particle collector outside the conduit is positioned so that a surface is perpendicular or approximately perpendicular to the axis of the funnel. A fan or other blower forces air through the funnel. A power supply imparts an electrostatic potential difference between the electrode, on the one hand, and the holder and particle collector, on the other hand. The electrostatic potential difference produces a corona field in the air in the vicinity of the electrode's sharp tip. The corona field imparts a charge to airborne particles. The combined effect of the air flow, electrostatic repulsion from the funnel and electrode, and electrostatic attraction toward the particle collector causes the airborne particles to move toward and then to adhere to the particle collector.

18 Claims, 2 Drawing Sheets

U.S. PATENT DOCUMENTS

| | | | |
|---|---|---|---|
| 6,156,103 A * | 12/2000 | Abdel-Rahman | 96/64 |
| 6,228,149 B1 * | 5/2001 | Alenichev et al. | 95/78 |
| 6,287,368 B1 * | 9/2001 | Ilmasti | 96/19 |
| 6,321,608 B1 | 11/2001 | Wagner et al. | 73/863.21 |
| 6,508,982 B1 * | 1/2003 | Shoji | 422/22 |
| 7,105,042 B2 * | 9/2006 | Tumbrink et al. | 96/96 |
| 2006/0021503 A1 * | 2/2006 | Thaler | 95/70 |
| 2007/0034025 A1 * | 2/2007 | Pant et al. | 73/863.21 |

OTHER PUBLICATIONS

Hinds, W. et al., "Sampling for inhalable aerosol," in *Particle Size-Selective Sampling for Particulate Air Contaminants*, J. Vincent (Ed.), pp. 119-140 (1998).

John, W. et al., "Sampling for respirable and fine aerosol," in *Particle Size-Selective Sampling for Particulate Air Contaminants*, J. Vincent (Ed.), pp. 155-167 (1989).

Mainelis, G. et al., "Collection of airborne microorganisms by a new electrostatic precipitator," *Aerosol Science*, vol. 33, pp. 1417-1432 (2002).

Mainelis, G. et al., "Collection of Airborne Microorganisms by Electrostatic Precipitation," *Aerosol Science and Tech*, vol. 30, pp. 127-144 (1999).

Mainelis et al., "Design and Collection Efficiency of a New Electrostatic Precipitator for Bioaerosol Collection," *Aerosol Science and Tech*, vol. 36, pp. 1073-1085 (2002).

Schneider, R. and E. Durr, "Ionic Spore Trap," Slide Show first presented publicly at Minneapolis, MN APS meeting (Jul. 28, 2008).

Schneider, R. et al., "A new spore trap that utilizes electrostatic deposition and scanning electron microscopy," Poster corresponding to APS Abstract (San Diego, Jul. 28-Aug. 1, 2007).

Yao, M. et al., "Utilization of natural electrical charges on airborne microorganisms for their collection by electrostatic means," *Aerosol Science*, vol. 37, pp. 513-527 (2006).

* cited by examiner

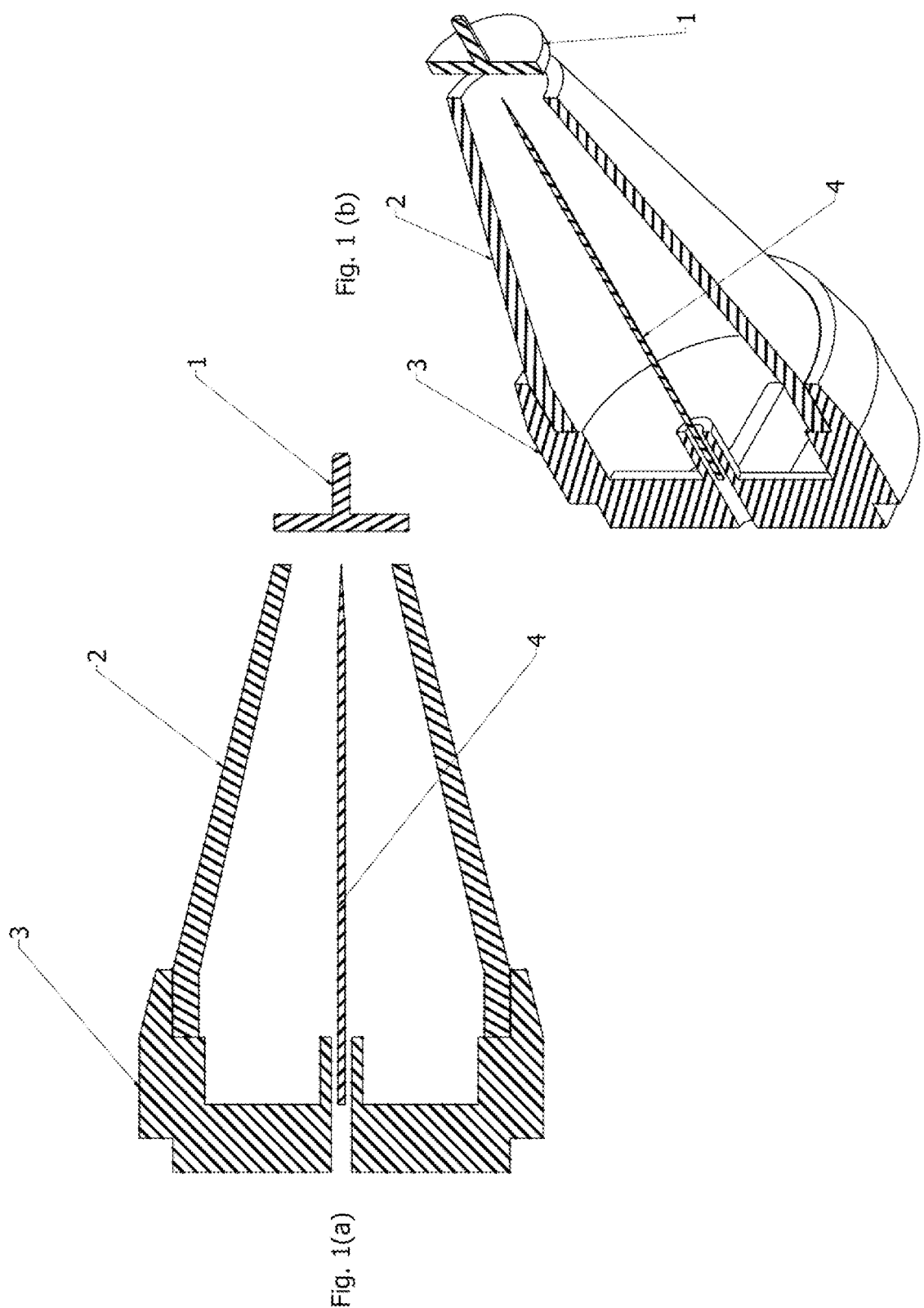

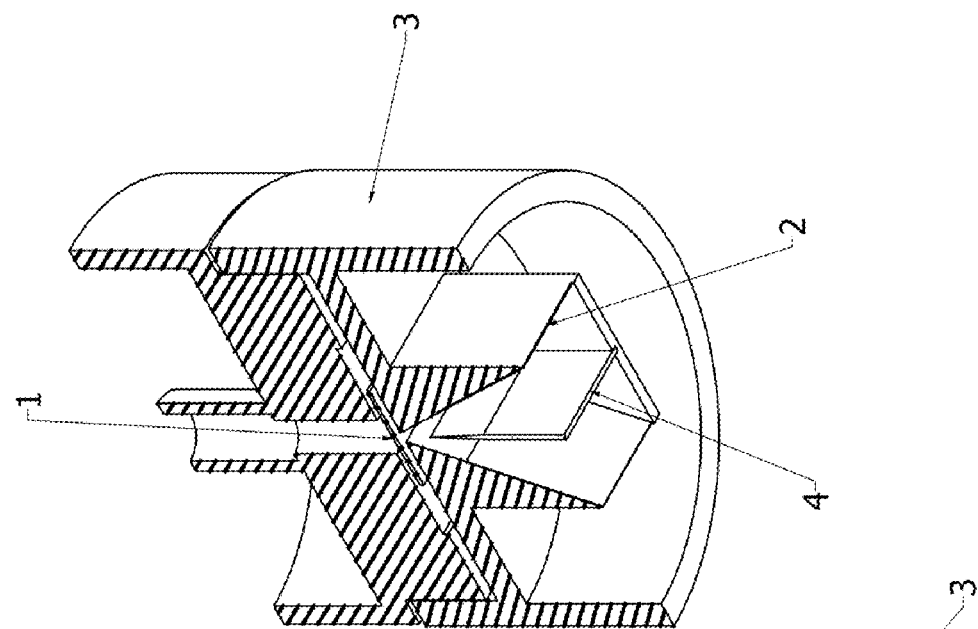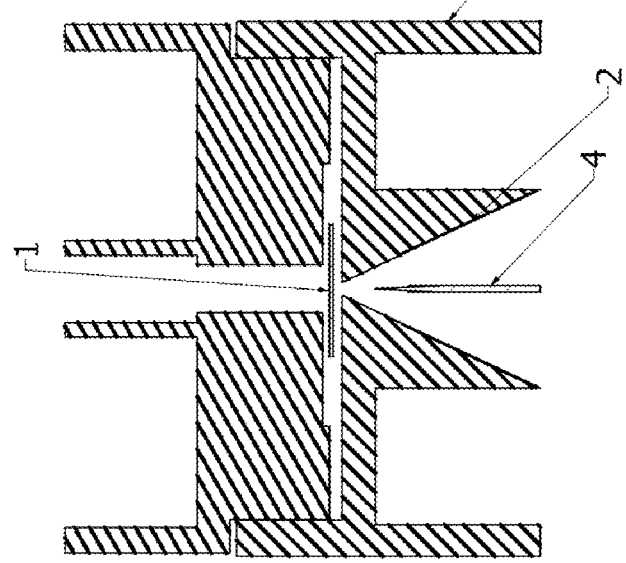

AIRBORNE PARTICULATE SAMPLER

The benefit of the filing date of provisional application Ser. No. 61/082,977, filed Jul. 23, 2008, is claimed under 35 U.S.C. §119(e).

The development of this invention was partially funded by the United States Government under grant number USDAS-CREES-Hatch-002297 awarded by the Department of Agriculture. The United States Government has certain rights in this invention.

This invention pertains to airborne particulate samplers, and to methods for collecting and analyzing airborne particulates.

There is an unfilled need for improved apparatus and methods to quantitatively sample airborne particulate matter. Several different fields could benefit from improvements in airborne sampling.

Airborne particulates include mold spores, other fungal spores; pollen; bacterial cells; bacterial spores; viruses; aerosols; exfoliated skin cells; scales, integument, and other materials from insects, mites, and other arthropods; pet dander; internal combustion engine exhausts, welding smoke, smoke stack exhaust, soot, and other combustion byproducts; other components of dust; meteorite dust; and many other types of biological and inorganic particulates.

Airborne particles that are less than 1 micrometer (micron) in diameter are sometimes called nanoparticles. Nanoparticles can be a public health concern because they can penetrate deep into lung tissue, where they can cause such chronic diseases as mesothelioma or asbestosis.

Inorganic particulates may be deliberately released into the air for military or terrorist purposes. Examples include radioactive dusts from so-called "dirty bombs"; or weaponized human, animal, or plant pathogens such as *Bacillus anthracis* (the anthrax organism), other bacteria, and viruses. The first step in detecting such threats is to capture the airborne particles so that they may be analyzed.

Public health would benefit from improved means to capture and concentrate airborne particles. Seasonal allergies are caused by airborne molds and pollen. In severe cases the allergies can lead to asthma. *Mycobacterium tuberculosis*, the causal agent of tuberculosis, is readily spread in air, and drug-resistant strains are becoming more widespread. Other infectious agents are also airborne, notoriously including influenza viruses. So-called "sick building syndrome" may be caused, at least in part, by certain molds that thrive in wet environments. The molds produce copious numbers of spores that are disseminated by building air handling systems. There is a pressing need to be able to qualitatively and quantitatively assess air for these organisms——*M. tuberculosis*, influenza viruses, spores of *Aspergillus, Penicillium, Stachybotrys*, other mold spores, etc.

"Quantitative" sampling means the accurate and reproducible measurement of particle density, e.g. the number of particles of a particular type per cubic meter of air. Where appropriate in context, "quantitative" sampling will generally (though not always) refer to the quantitative sampling of a specified particle type, rather than total particles of all types.

The microscopic identification and quantification of fungal spores, such as those of *Phakopsora pachyrhizi*, the soybean rust pathogen, in environmental samples, spore traps, and laboratory specimens has previously presented a challenge to workers. Prior reports, particularly involving passive and impact spore traps, have commonly described the number of "rust-like" spores, without further detail. For other forensic samples, visualization has often been difficult or even impossible amidst the accompanying milieu of dust, pollen, and spores from other fungal species.

Previous airborne particle sampling devices have included primarily those based upon filter membranes, impact samplers, perforated disc samplers, passive samplers, and electrostatic precipitators.

Filter membranes. Particulates are drawn through a filter by a vacuum pump. The filter medium has pore sizes that allow air to pass but trap particulates within a certain size range. Filters are typically operated only for relatively short times before the filter substrate clogs. Filter-based devices are often used indoors to sample for toxic, abiotic particles, such as heavy metals, PAHs, or other toxins. The filter, together with its trapped particles, may be subjected to chemical analyses. Alternatively, the capture medium may be analyzed by immunological means. However, direct microscopic examination of the filter substrate is problematic due to its thickness, opacity, and fibrous substrate. Filters are most efficient with relatively large pore sizes, so that air may be drawn through the device. Filters are difficult or inefficient to use for sampling nanoparticles due to their particle size limitations.

Impact samplers. Impact samplers are perhaps the mostly commonly used devices for bioaerosol monitoring, particularly for collecting fungal spores. Plastic impact sampling cassettes have been used by industrial hygienists, but these devices are strongly biased toward collecting particles with diameters greater than a few microns. They tend to underestimate smaller particles due to aerodynamic properties. The surface boundary layer of air around the impact collection surface inhibits the capture of small particles with low momentum. The boundary layer causes smaller particles to easily be swept out of the collection device, without ever contacting the collector.

In a typical impact sampler, particulates are drawn through an orifice by a vacuum pump. The air flow impacts onto a transparent material (glass slide or transparent tape) that has been coated with an adhesive material, to which particles adhere. The capture medium can then be viewed with a standard microscope. A disadvantage of this approach is that simple microscopic examination often does not allow one to identify organisms to the species level, nor in some cases even to the genus level. Also, because capture efficiency is generally low for smaller particles, viruses, bacteria, and small fungal spores may be undercounted or missed entirely. These devices are generally not well-suited for modern analytical procedures such as quantitative PCR assays for specific organisms, nor for chemical analyses of inorganic particles. While the surfaces can supply a relatively small area on which particles are captured, there are significant limitations on air flow and capture efficiency, related to the physical principles of impact from a moving air stream. Much of the air and the airborne particles will flow over the capture site without actually contacting it. Impact collectors rely on the momentum of the particles to overcome boundary-layer, fluid-flow effects adjacent to the capture medium. If the particle is not sufficiently dense, it can simply remain in the airstream and be evacuated from the device, without ever contacting the capture medium. Capture efficiency with impact devices declines precipitously as the particle size decreases. Bacterial cells, small fungal spores, e.g. *Aspergillus* spp. and *Penicillium* spp., and nanoparticles can be missed entirely.

Perforated disc samplers. A vacuum pump draws air through a metal disc that has perforations sized to exclude particles above a cutoff size, but to allow smaller particles to pass through where they may be deposited onto a growth medium, such as agar. Bacteria and fungal spores can germinate, and those organisms that will grow on the medium may be identified by standard techniques. However, faster-growing organisms can mask the presence of slower-growing ones, and relatively few selective media are available. Nonviable organisms and those that do not grow well on the particular medium will not be detected by this method. This technique is generally used to monitor populations of specific organisms for which selective media are available. These devices are usually operated for very short periods of time, because the capture media can quickly be overgrown with bacteria and fungi.

Passive samplers. Gravity or air currents cause particles to settle onto a sampling surface. These devices use neither forced air flow nor other active means to enhance collection efficiency. For example, a personal monitoring device has been described that is designed to be worn by an individual, including a scanning electron microscope (SEM) mount protected by a screen. Particles are passively deposited on the mount, and the mount is later viewed with a SEM.

Electrostatic precipitators. Air is drawn into a chamber in which particulates are charged in a high-voltage field. The charged particles are electrostatically deposited onto agar plates. While capture efficiencies can be relatively high, the particles are captured on a relatively large surface, and again the microbes must germinate and grow before they can be identified. This technique is not well-suited for microscopic examination. The large capture surface area, and the semi-solid capture medium make quantitative PCR analyses difficult to perform, because a large volume of extraction buffer would be needed to process the entire capture medium.

A variation of the electrostatic precipitator is a device that imposes a high voltage on a continuous stream of water. The water acts as an electrostatic capture medium, and traps airborne particles. The water is then collected and assayed, for example by PCR. This technique is not well-suited for microscopic examination, nor for the efficient capture of inorganic particles.

Electrostatic precipitation of particulates has long been used to clean air in industrial settings, for example to scrub particulate pollutants from smoke stack emissions. These devices generally collect the particulates and dispose of them; they are neither designed nor typically used for analytical or monitoring purposes.

For analytical and monitoring purposes, electrostatic capture electrodes in earlier devices have been bathed in flowing liquid, or have employed large surfaces for collecting microbes, for example on agar plates. United States patent application publication no. 2007/0034025 A1 described a device in which a conical charging or ionizing electrode formed the outer wall of a duct to conduct air through the device. Particulates were collected on an oppositely-charged inner cylindrical electrode (15 mm in diameter). Two methods were described for recovering the collected particles for analysis: The electrode is bathed with water, buffer or oil during operation, and the liquid is collected in a reservoir where it can be sampled for analysis; or particulates are wiped, scraped, or blown from the surface of the collection cylinder. It is not clear that either approach is well-suited for quantitative analysis.

In other reported devices the collection electrode has had a relatively large surface, to which agar-filled Petri dishes may be attached.

M. Yao et al., "Utilization of natural electrical charges on airborne microorganisms for their collection by electrostatic means," *Aerosol Science*, vol. 37, pp. 513-527 (2006) described a device in which microbes were attracted to an electrode on the basis of the microbe's own inherent, pre-existing electrical charge.

G. Mainelis et al., "Collection of airborne microorganisms by a new electrostatic precipitator," *Aerosol Science*, vol. 33, pp. 1417-1432 (2002); G. Mainelis et al., "Collection of airborne microorganisms by electrostatic deposition," *Aerosol Science*, vol. 30, pp. 127-144 (1999); and G. Mainelis et al., "Design and collection efficiency of a new electrostatic precipitator for bioaerosol collection," *Aerosol Science*, vol. 36, pp. 1073-1085 (2002) described a device that draws particles into a sampling chamber and imparts a charge to them with a thin wire stretched across the opening and placed at a potential of 4,000 volts. The charged particulates, including fungal spores and bacterial cells, were then attracted to agar plates having an opposite charge. These devices are not well-suited to identify organisms other than those that readily germinate and grow on agar plates.

A limitation common to most current techniques is that they are generally able to handle only low air flow rates (~10 liters per minute or less). Capture efficiencies decline, often dramatically, if higher flow rates are used. Further, there is no single existing device that is well-suited for use with a full range of analytical procedures on the captured particulates; e.g., a device whose output is readily observed microscopically is not well-suited for PCR analysis or for growth of cultures; and a device whose output is well-suited for growth of cultures does not readily lend itself to microscopic observation.

U.S. Pat. No. 5,243,864 discloses a device that employs a tacky surface to trap airborne particles.

U.S. Pat. No. 6,321,608 discloses a passive aerosol particle sampler in which the collection surface is an electron microscopy mount with a mesh cover.

R. Schneider et al., "A new spore trap that utilizes electrostatic deposition and scanning electron microscopy," APS Abstract (San Diego, Jul. 28-Aug. 1, 2007), *Phytopathology* 97:S105 is an early report from our research group. The precise date when this Abstract became available to conference participants is not currently known, but it may have been in June 2007. The Abstract describes some, but not all, aspects of the novel device. A copy of the Abstract was included as Appendix A in provisional priority application 61/082,977. The corresponding poster is included as Appendix B in the provisional priority application. The poster was first presented to the public on Jul. 29, 2007.

R. Schneider and E. Durr, "Ionic Spore Trap," was a slide show by the present inventors, first presented publicly on Jul. 28, 2008 at the APS meeting in Minneapolis.

S. Grinshpun et al., "A small change in the design of a slit bioaerosol impactor significantly improves its collection characteristics," *J. Environ. Monit.*, vol. 9, pp. 855-861 (2007) discloses a slit jet design for an impact sampler for bioaerosol monitoring, and also mentions some of the other configurations that have been used for impact samplers.

W. Hinds et al., "Sampling for inhalable aerosol," pp. 119-140 in J. Vincent (Ed.), *Particle Size-Selective Sampling for Particulate Air Contaminants* (1999); and W. John et al., "Sampling for respirable and fine aerosol," pp. 155-167 in J. Vincent (Ed.), *Particle Size-Selective Sampling for Particulate Air Contaminants* (1999) provide reviews of various techniques used for sampling aerosols, particularly inhalable particles.

We have discovered a novel airborne particulate sampling device and method that overcomes the limitations noted above. The device includes a conduit for the flow of air. In preferred embodiments the conduit is tapered, and has for example the shape of conical funnel or a V-shaped trough; in these preferred embodiments air enters at the wider end and exits through a relatively small opening, at a higher velocity, at the narrower end. It is not required that the air conduit be tapered, however; it could also assume other shapes, such as a simple pipe with a constant, circular cross section. The conduit, or at least its surface, is an electrical conductor. The device also includes an electrode with a sharp tip or sharp edge (e.g., a needle or a razor blade) positioned near the output side of the conduit. A holder positions an electrically conducting particle collector (e.g., an electron microscopy mount) outside the conduit, near the output side of the conduit, such that a surface of the particle collector is perpendicular or approximately perpendicular to the direction of air flow exiting the conduit. A fan or other blower forces air through the conduit. The design of the novel device allows it to process a much higher volumetric air flow rate than any prior device known to the inventors. A power supply imparts an electrostatic potential difference between the electrode, on the one hand, and the holder or particle collector, on the other hand. The DC potential is preferably pulsed. The pulsed field from the electrode induces a field of smaller magnitude on the conduit (or at least on the conducting surface of the conduit.) In operation, the blower forces air with airborne particles through the conduit, from the input side towards the output side, and thence to the particle collector. The electrostatic potential difference between the electrode and the conduit, on the one hand, and the holder or particle collector, on the other hand produces a corona field in the air in the vicinity of the electrode's sharp tip or edge. The corona field imparts a charge to airborne particles. The cross-sectional dimensions of the conduit in the vicinity of the electrode should be such that substantially all airborne particles in the vicinity of the electrode experience a sufficiently high electric field that they become charged. (The dimensions of the output opening should also approximately match the dimensions of the collector—for example, a typical SEM mount is circular with a diameter of approximately 2.5 cm. As a practical matter, the larger the dimensions of the output opening are, the higher the electrical potential that will be needed to generate a corona field that would extend throughout the output opening.) The combined effect of the airflow, electrostatic repulsion of the charged particles from the conduit, and electrostatic attraction toward the particle collector causes the airborne particles to move toward and then to adhere to the particle collector. It is preferred to place a thin adhesive layer on the collector. The collector may be flat or smoothly curved; however, it should not contain rough edges, surfaces, or irregularities that could lead to a high electric field or cause arcing.

A distinct advantage of the present invention is that it can process large volumes of air, while trapping even very small particles efficiently. With very small particles (on the order of 1 μm or smaller), the principle force initially driving the particles from the conduit toward the collector is that from the airflow. As the particles approach the collector, electrostatic attraction predominates, and pulls the particles through the boundary layer and onto the surface of the collector. In the absence of the electrostatic attraction, the boundary layer would deflect the vast majority of the smaller particles, and they would not be collected efficiently. In the absence of the blower, electrostatic attraction alone could not process large samples of air rapidly. The combination of these two features, a blower to move large volumes of air relatively rapidly, and electrostatic attraction to pull small particles through the boundary layer to the collector surface, provides an unexpected synergism and offers substantial advantages that would not have been predicted from the individual properties of the two features considered separately.

The novel device may be used to efficiently sample much higher air flow rates than has previously been possible. For example, a prototype embodiment employed a high capacity exhaust fan that drew air into the device at more than 600 liters per minute. Even faster rates should be possible. The ability to process high flow rates is very helpful for assessing airborne particulates that may be present at low densities, e.g., 1-10 particles per cubic meter.

In a prototype embodiment, a small disk, ~1 inch (~2.5 cm) diameter, was used as the capture surface. Different capture media were affixed to the capture surface, for example: (1) Carbon-coated adhesive discs may be used for scanning electron microscopy for high resolution imaging of the captured particles, or for energy dispersive spectroscopy, which is used for chemical analyses of individual captured particles. This capture medium may also be used for immunofluorescent assays of specific organisms with an incident light fluorescence microscope. (2) Clear adhesive tape, which is easily removed from the capture surface, and which may be used for light microscopy or for PCR. Spores and pollen are readily removed from the adhesive medium, for example with commercially available qPCR (quantitative PCR) kits. An adhesive tape medium, in combination with qPCR, allows for highly reproducible quantitative analyses of specific organisms to the species or even subspecies level. This capture medium may also be used for immunofluorescence microscopy with a transmitted light fluorescence microscope. (3) Culture medium, e.g., agar medium, which may be used to assess viability of culturable organisms shortly after they are captured in the device.

The device concentrates particles by first using a blower to direct the airstream through a conduit, from the "mouth" or "input side" towards the "throat" or "output side." In preferred embodiments, the conduit is tapered to increase the rate of air flow at the output side of the conduit, e.g. a funnel or trough shape. A needle, wire, blade (razor blade), or other conductor with a sharp tip or sharp edge in or near the output side of the conduit is placed at a high voltage, e.g., 1000 V or 2000 V, up to 7000 V or 10,000V, but not so high as to cause dielectric breakdown of the air. This conductor has a sharp tip or edge, to increase the electric field in its vicinity, to produce a "corona" field. As the air passes through the output side it passes through the high electric field in the vicinity of the electrode's tip or edge. The concentrated, corona field at the sharpened end of the electrode causes the particles to become charged. The pulsed field from the electrode induces a field of smaller magnitude on the conduit (or at least on the conducting surface of the conduit.) The charged particles then exit the throat with the airstream, and are captured on the oppositely charged (or grounded) collection surface. This collection surface is preferably ~1 inch (~2.5 cm) in diameter or smaller, and should be easily removable from the device for analysis after collection of particles. Circular SEM mounts of various sizes are preferred collection surfaces. It is preferred that the size of the conduit's exit should be about the same size as the collection surface, to promote efficient capture of particles. Preferred voltage is ~7000V, with a preferred gap between electrode and collector of ~0.75 cm. (A rule of thumb is to set the potential ~1000V below the dielectric breakdown of air, accounting for electrode geometry.) It is usually preferred to place the electrode at a negative potential relative to the collector, although in some applications the electrode potential might instead be positive.

Advantages of the novel electrostatic sampler, or of optional embodiments of the novel device, include one or more of the following: (1) Airborne particulate matter can be captured on a mount that may be easily removed from the unit and processed for scanning electron microscopy, light microscopy, fluorescence microscopy, or real-time PCR.

Alternatively, an absorbent membrane can be affixed to the mount, and spore germination can be assessed by incubating the mount under appropriate conditions. (2) The device can optionally be made programmable by interfacing it with a computer. The user may control the hours of the day, and the days of the week during which the device operates. The fan speed can be controlled. (3) The device can record humidity and temperature, and transfer those measurements to a computer. (4) A prototype device was capable of efficiently processing air at a rate of about 40 cubic feet per minute (about 1100 liters per minute) when the exhaust fan was set at 100% power. Subsequent embodiments can be designed to operate at higher or lower flow rates, as appropriate for particular uses. The ability to efficiently separate and process particles at such high volumetric flow rates is a distinct advantage over most (and perhaps all) prior devices. This ability allows one to better detect particles that may be present in very low concentrations. (5) A preferred embodiment is constructed of stainless steel to allow it to operate under adverse weather conditions. (6) Organisms, spores, and pollen may be identified based on their morphology. (7) Trapping efficiency can be very high: preferably at least 80%, more preferably at least 90%, most preferably at least 95%, and in some cases approaching ~100%. (8) There is no need for microbial culturing, although captured samples may be cultured if desired. Non-culturable organisms, pollen, and spores may be identified by morphology or PCR. (9) A device in accordance with the present invention may be inexpensive, and can run unattended for long periods. (10) The present invention is well-suited for carrying out both qualitative and quantitative analyses.

Optionally, microscopic analysis may be partially or fully automated using machine vision software otherwise known in the art.

BRIEF DESCRIPTION OF THE DRAWINGS

FIGS. 1(a) and 1(b) depict a prototype embodiment of the novel electrostatic sampler, using a funnel conduit and a needle electrode.

FIGS. 2(a) and 2(b) depict a prototype embodiment of the novel electrostatic sampler, using a trough conduit and a razor blade electrode.

EXAMPLE 1

Prototype Embodiment

A prototype embodiment that we have built and successfully tested is depicted in FIGS. 1(a) and 1(b). Scanning electron microscope mount 1 acted as the collector, and was held in place by a specimen holder (not shown). It is highly recommended that collector 1 be electrically grounded, to reduce the risk of electrical shock to the user (a risk to which the inventors can personally attest). (In an alternative embodiment, the collector itself need not necessarily be electrically conductive if it has an electrically-conductive coating that may be grounded—for example, a coated glass microscope slide, using a strip of foil or wire to ground the coating—or even if a conductor is positioned directly underneath a thin glass slide. The slide may then be used directly for light microscopy.) Funnel 2 directed the air flow from a fan or blower (not shown). Our experiments showed that substantially better results were obtained when the funnel was made of an electrically conducting material rather than a dielectric insulator. The induced charge on the conducting funnel helped focus particles towards the center. Mount 3 supported both funnel structure 2 and electrode 4, but was not in electrical contact with electrode 4. High voltage electrode 4 had a sharp tip on the end closest to collector 1, to produce a high-electric-field corona discharge. The other end of electrode 4 was connected to a high-voltage pulsed DC power supply (not shown). While the funnel or other conduit may be directly connected to the power supply, it need not be. It is preferred instead to induce a potential on the conduit by its proximity to the electrode; typically, the induced voltage on the funnel is ~60% to ~80% of the electrode voltage, depending on geometry and proximity.

We have also tested several other possible designs, and found that superior results were obtained with the novel conducting funnel/conducting needle configuration. In future tests, we plan to test a V-shaped trough with a narrow slit exit, using a razor blade to provide a sharp edge for the electrode. This alternative embodiment, not yet built, is depicted in FIGS. 2(*a*) and 2(*b*). The parts generally correspond to like-numbered parts in FIGS. 1(*a*) and 1(*b*), except that electrode 4 is a razor blade with a sharp edge, and conduit 2 is a trough with a slit opening.

It is preferred that the direction of travel of the charged particles onto the surface of collector 1 should be perpendicular, or nearly perpendicular, as a perpendicular impact appears to be most efficient for trapping small particles. Smaller particles can be swept away from the collector surface by air flow, so it is preferred to keep their direction of travel nearly perpendicular to the collector surface.

In the prototype embodiment, electrode 4 was placed at a potential between 1000 and 7000 volts using a pulsed direct current transformer operating at 15 to 20 kHz. The gap between mount 1 and electrode 4 was adjustable from 0.60 to 2.50 cm.

EXAMPLE 2

Operation of the Prototype Embodiment

Air with particulate matter was drawn in through the large opening of stainless steel funnel 2 by an electric exhaust fan (not shown). Electrode 4 was charged to the selected voltage (1,000-7,000 volts) with the pulsed transformer. (A voltage that is too high can disrupt spores or other cells, or cause dielectric breakdown of air. A voltage that is too low can lead to less efficient capture of particles.) Placing a high potential on electrode 4 had the following desirable consequences: it impressed a charge of the same polarity on the particulates, it caused the charged particles to be repelled from conducting funnel 2 and from electrode 4 through the constricted end of the funnel 2 towards collector 1, and it caused the particles to space themselves from one another by mutual electrostatic repulsion, allowing better identification and quantification of the collected particles. Collector 1 is optionally covered with one of several types of membranes or adhesives known in the art, for example an electrically conductive adhesive disc for use with a scanning electron microscope, or double-sided clear adhesive tape for light microscopy with a compound microscope or for immunofluorescent microscopy. Collector 1 was retained in a specimen holder (not shown), which was electrically grounded along with a specimen holder receiver socket (not shown). The specimen holder was easily removed from the specimen holder receiver socket by the operator with a simple twisting motion, and collector/SEM mount 1 could then easily be withdrawn from specimen holder receiver socket for analysis.

EXAMPLE 3

Testing and Performance of the Prototype Electrostatic Sampler

The prototype electrostatic sampler has been successfully tested in the laboratory, in agricultural fields, and in industrial facilities. Laboratory tests evaluated different capture substrates affixed to the sample mount, including petrolatum gel, a commercial spray-on adhesive, a commercial liquid adhesive with suspended carbon black particles, a commercial double-sided clear adhesive tape, a nitrocellulose membrane, and an electrically conductive adhesive disk.

Each type of substrate was individually affixed to the sample mount, the mount was installed in the electrostatic sampler, and the sampler was operated for two hours at midday in a soybean field known to be heavily infected with *Phakopsora pachyrhizi*, the fungal pathogen that causes soybean rust. The substrates were removed from the device and assessed for capture efficiency by scanning electron microscopy. These tests were repeated four times, with similar results. The highest number of particulates, including spores of different fungal species, was found on the electrically conductive adhesive disks. A clear double-sided tape (3M® Model 666) also performed very well. The double-sided tape was affixed to a glass microscope slide and the adhering spores and other particles were readily viewed with a compound light microscope.

EXAMPLE 4

Further Testing in Soybean Fields

The device was field-tested in Quincy, Fla. and Baton Rouge, La., from March through September of each of 2007 and 2008. Those tests that were not conducted directly by one or both of the inventors were undertaken pursuant to a written confidentiality agreement. The principal purposes of these tests were twofold: (1) to test the ability of the prototype embodiment to perform properly when used under field conditions; and (2) to determine whether spores of the soybean rust pathogen, *Phakopsora pachyrhizi*, could be detected well before disease symptoms appeared on soybean plants in the immediate area. Also included in the tests for comparative purposes were a commercial impact sampler (the Burkard® 7-day Recording Sampler) and a conventional rain water collector. Rain water samples were assayed by real-time polymerase chain reaction (R-T PCR), a very sensitive protocol that can detect as little as a single fungal spore.

The electrostatic sampler detected *P. pachyrhizi* in late May of each year, at the Florida and Louisiana locations, about 5 weeks before the first outward appearance of disease symptoms on any soybean plants in the immediate area. Detection was by direct observation of the capture mount via scanning electron microscopy. Immunofluorescent assays were successfully conducted with subsamples. Each device was sampled on a weekly schedule, from mid-March to mid-September. The impact sampler and the rain water sampler only detected the pathogen after disease symptoms had been observed macroscopically, implying that they were substantially less efficient at capturing spores in this test. The results from the electrostatic sampler were clearly superior in these tests.

EXAMPLE 5

Confirmation of Sensitivity by PCR

Further testing was conducted to assess the detection sensitivity of the prototype embodiment. The electrostatic sampler was placed in a biosecurity hood to prevent accidental contamination. A single spore of *P. pachyrhizi* was collected onto the tip of an eyelash, and then released into the intake air stream generated by the exhaust fan of the device. Protocols for detecting *P. pachyrhizi*, using both standard PCR and quantitative PCR (Q-PCR), are available, and have proven useful in discriminating *P. pachyrhizi* from other rust fungi, and for quantifying DNA and the spore numbers. See J. Haudenshield et al., "Quantification and single-spore detection of *Phakopsora pachyrhizi*," Proceedings of the National Soybean Rust Symposium (Dec. 12-14, 2007, Louisville, Ky.), available at:
http://www.plantmanagementnetwork.org/infocenter/topic/soybeanrust/2007/posters/17.asp J. Haudenshield et al. developed and validated a combined method for DNA extraction and analysis by Q-PCR that reliably detects, identifies, and quantifies small numbers, even single spores, of *P. pachyrhizi*. The same protocol was successfully used on single-spore samples collected with the novel electrostatic sampler, and also with small numbers of spores. The results showed that the electrostatic sampler was extremely sensitive and quantitative in detecting and measuring numbers of spores per cubic meter of air (data not shown).

EXAMPLE 6

Capture of Inorganic Particles in a Commercial Manufacturing Facility

Additional testing was conducted in a commercial manufacturing facility where gas metal arc welding, gas tungsten arc welding, and grinding were in progress. The principal purpose of these tests was to assess the sampler's ability to quantitatively detect airborne particulates resulting from these operations, including welding smoke. The sampler was fitted with carbon-coated adhesive disks, and it was then operated for various periods of time in close proximity to the manufacturing operations. The sample mounts were then observed with a scanning electron microscope (SEM), and the captured particulates were counted. In one sampling run from a welding operation, we measured 73.3 million particles per liter of air, particles ranging in size from less than 300 nanometers to about 1 micron in diameter. Randomly-selected particles were photographed by SEM and simultaneously subjected to energy dispersive spectroscopy (EDS) within the electron microscope. The SEM with an EDS analytical attachment allows the operator to direct a high energy electron beam at a particle of interest and measure the resulting dispersed energy spectrum, which is a function primarily of the particle's elemental composition. Individual particles were photographed and categorized as a function of shape and elemental composition. Particles from a molten source were readily distinguished by their spherical shapes. The following elements were qualitatively observed in the welding smoke: iron, chromium, silicon, manganese, calcium, copper, tungsten, and sulfur. Each of these elements is a component of standard welding rods.

In another test, airborne dust from a grinding wheel that was being used to grind stainless steel was sampled, viewed, and analyzed as described above. Particles from the grinding operation were readily identified by their sharp edges, with diameters (i.e., the widest dimensions) ranging from ~750 nm to ~2 μm. Of particular significance was our finding that we could quantify particles less than 1 micrometer in diameter in a repeatable manner. Particles of this size range, or "nanoparticles," can pose health hazards because they can penetrate deep into lung tissue. The novel electrostatic sampler is the only device known to the inventors that is capable of quantitatively assessing such particulates in air, and of providing chemical analytical capability for individual particles. It has not previously been possible to capture nanoparticles in a manner that simultaneously allows for both microscopic examination and chemical analysis.

EXAMPLE 7

Capture of Inorganic Particles from Diesel Exhaust

The prototype sampler was also tested for its ability to capture and analyze particulates from diesel engine exhaust. The sampler was operated for 15 seconds within the smoke plume of a diesel tractor exhaust stack. The sample mount was then examined with a scanning electron microscope, and individual particles were assayed by EDS analysis. Readily identifiable and quantifiable particulates were observed. Their chemical composition was primarily carbon and sulfur. Diesel exhaust particulates were readily identifiable by a snowflake-like appearance. The inventors are not aware of any other device that captures diesel exhaust particulates in a form that can be readily documented microscopically.

Miscellaneous

In summary, the prototype electrostatic sampler was able to detect spores with very high sensitivity (even a single fungal spore) and very high specificity. The captured spores could be identified to the species level using a variety of analytical protocols including light microscopy, immunofluorescent microscopy, scanning electron microscopy, and real-time polymerase chain reaction assays. The prototype electrostatic sampler was also capable of quantitatively assessing abiotic nanoparticles, and these particles could then be analyzed for chemical composition. All of these functions were performed with the same instrument. No other device known to the inventors is as versatile, quantitative, sensitive and specific as the electrostatic sampler described here.

The device may optionally be powered by a 12-volt battery, or a transformer connected to a source of alternating current, a solar cell, or other power supply.

In an alternative embodiment, a sample changer is provided, allowing for different collectors to be exposed at different times. A changer might, for example, have a vertical stack configuration, or a rotating carousel configuration.

When the device is used in the field, it is preferred to provide a covering to protect it from rain, while still permitting air to flow freely in its vicinity, for example covering it with a rain-out dome.

When used in the field, the device optionally but preferably also includes instrumentation to record other pertinent factors, such as time, date, temperature, humidity, fan speed, voltage, etc., to assist the user in better interpreting data.

The complete disclosures of all references cited in this specification are hereby incorporated by reference, including the complete disclosure of the priority provisional applications. In the event of an otherwise irreconcilable conflict, however, the present specification shall control.

We claim:

1. A device for collecting airborne particles, wherein said device comprises:
   (a) a conduit having an input and an output; wherein the interior of said conduit is adapted to allow the flow of air from the input to the output; and wherein said conduit comprises an electrical conductor, or the surface of said conduit comprises an electrical conductor;
   (b) an electrode with a sharp tip or a sharp edge; wherein said sharp tip or sharp edge is positioned on or near the output of said conduit; wherein said electrode is not in electrical contact with said conduit; wherein said electrode is adapted to produce a corona field in air in the vicinity of said sharp tip or sharp edge when a sufficiently high electrical potential is applied to said electrode;
   (c) a holder that is adapted to hold an electrically conducting particle collector outside said conduit, near the output of said conduit, such that at least one surface of said particle collector is perpendicular to or approximately perpendicular to the direction of airflow from the output of said conduit;
   (d) a blower that is adapted to force air through said conduit, from the input towards the output and thence to the particle collector;
   (e) a power supply that is adapted to impart a pulsed DC electrostatic potential difference between said electrode, on the one hand, and said holder or the particle collector, on the other hand; wherein the DC electrostatic potential is sufficiently high to produce a corona field in the vicinity of said sharp tip or sharp edge of said electrode; wherein the corona field is at least about 2000 V/cm and is below the dielectric breakdown of air under ambient conditions;
   wherein, during operation, said device is adapted to collect airborne particles in the following manner:
   said blower forces air with airborne particles through said conduit, from the input towards the output and thence to the particle collector; said power supply imparts a pulsed DC electrostatic potential difference between said electrode, on the one hand, and said holder or the particle collector, on the other hand; the resulting pulsed charge on the electrode induces an electric field on said conduit or on the conducting surface of said conduit; the DC potential difference produces a corona field in the air in the vicinity of said electrode's sharp tip or sharp edge, wherein the corona field is at least about 2000 V/cm and is below the dielectric breakdown of air under ambient conditions; the corona field imparts a charge to airborne particles in the vicinity of said electrode; the combined effect of the air flow and electrostatic effects cause charged airborne particles to move from the output of said conduit toward the particle collector; and electrostatic attraction causes particles to contact the particle collector, including particles that would be too small, in an otherwise identical device operated in an otherwise identical manner, but without the electrostatic potential difference and without the corona field, to penetrate the boundary layer of air over the surface of the collector and that would therefore be swept away without contacting the particle collector.

2. The device of claim 1, wherein said conduit has the shape of a conical funnel, and wherein said electrode has the shape of a needle with a sharp tip.

3. The device of claim 1, wherein said conduit has the shape of a V-shaped trough, and wherein said electrode has the shape of a blade with a sharp edge.

4. The device of claim 1, additionally comprising an electrically conducting particle collector.

5. The device of claim 4, wherein said particle collector is adapted for use as a sample mount in an electron microscope.

6. The device of claim 4, wherein said particle collector comprises an adhesive layer to which captured particles will adhere.

7. A method for collecting airborne particles with the device of claim 4; wherein said method comprises the steps of:

(a) forcing air with airborne particles from the blower through the conduit, from the input towards the output and thence to the particle collector;

(b) imparting a pulsed DC electrostatic potential difference from the power supply between the electrode, on the one hand, and the holder or the particle collector, on the other hand; wherein the resulting pulsed charge on the electrode induces an electric field on the conduit or on the conducting surface of the conduit; and wherein the potential difference produces a corona field in the air in the vicinity of the electrode's sharp tip or sharp edge, wherein the corona field is at least about 2000 V/cm and is below the dielectric breakdown of air under ambient conditions; and wherein the corona field imparts a charge to airborne particles in the vicinity of said electrode;

wherein:

(c) the combined effect of the air flow and electrostatic effects cause charged airborne particles to move from the output of the conduit toward the particle collector; and electrostatic attraction causes particles to contact the particle collector, including particles that would be too small, in an otherwise identical device operated in an otherwise identical manner, but without the electrostatic potential difference and without the corona field, to penetrate the boundary layer of air over the surface of the collector and that would therefore be swept away without contacting the particle collector.

8. The method of claim 7, wherein the conduit has the shape of a conical funnel, and wherein the electrode has the shape of a needle with a sharp tip.

9. The method of claim 7, wherein the conduit has the shape of a V-shaped trough, and wherein the electrode has the shape of a razor blade with a sharp edge.

10. The method of claim 7, wherein the particle collector is adapted for use as a mount in an electron microscope.

11. The method of claim 7, wherein the particle collector comprises an adhesive layer to which particles will stick.

12. The method of claim 7, wherein at least some of the particles have a diameter smaller than 1 μm.

13. The method of claim 7, wherein the particles comprise fungal spores.

14. The method of claim 7, wherein the particles comprise pollen, bacteria, or viruses.

15. The method of claim 7, wherein the particles comprise abiotic particles produced as a byproduct at an industrial facility.

16. The method of claim 7, wherein the particles comprise meteorite dust.

17. The method of claim 7, additionally comprising the step of analyzing the collected particles by one or more techniques selected from the group consisting of light microscopy, fluorescence microscopy, electron microscopy, amplification by polymerase chain reaction, and culturing bacteria within the particles.

18. The method of claim 7, wherein the blower forces air through the conduit at a rate of at least about 1000 liters per minute; and wherein at least about 80% by mass of the airborne particles are captured by the particle collector.

* * * * *